(12) United States Patent
Cha et al.

(10) Patent No.: US 11,300,554 B2
(45) Date of Patent: Apr. 12, 2022

(54) CALCITE CHANNEL STRUCTURES WITH HETEROGENEOUS WETTABILITY

(71) Applicant: Saudi Arabian Oil Company, Dhahran (SA)

(72) Inventors: Dong Kyu Cha, Abqaiq (SA); Ahmed Gmira, Al-Khobar (SA); Mohammed Badri AlOtaibi, Abqaiq (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 135 days.

(21) Appl. No.: 16/742,644

(22) Filed: Jan. 14, 2020

(65) Prior Publication Data

US 2021/0215658 A1  Jul. 15, 2021

(51) Int. Cl.
*B81C 1/00* (2006.01)
*G01N 33/28* (2006.01)
*B81B 1/00* (2006.01)
*G01N 13/00* (2006.01)

(52) U.S. Cl.
CPC .......... *G01N 33/2823* (2013.01); *B81B 1/00* (2013.01); *B81C 1/00531* (2013.01); *G01N 13/00* (2013.01); *B81B 2201/058* (2013.01); *B81B 2203/0338* (2013.01); *B81C 2201/0132* (2013.01); *B81C 2201/0159* (2013.01)

(58) Field of Classification Search
CPC ................................................ B81C 1/00531
See application file for complete search history.

(56) References Cited

U.S. PATENT DOCUMENTS

| 4,564,997 | A |   | 1/1986  | Matsuo |
| 4,882,763 | A | * | 11/1989 | Buchan .................. G09B 23/08 382/109 |
| 5,464,473 | A | * | 11/1995 | Shiao .................... C04B 28/001 106/811 |
| 6,489,405 | B1 | * | 12/2002 | Beisele ................. C08G 59/12 428/413 |
| 10,365,564 | B2 |  | 7/2019  | Cha et al. |

(Continued)

FOREIGN PATENT DOCUMENTS

| WO | 2009149362 | 12/2009 |
| WO | 2017009710 | 1/2017 |

(Continued)

OTHER PUBLICATIONS

Becker et al., "Polymer microfluidic devices," Talanta, vol. 56, No. 2, Feb. 11, 2002, 21 pages.

(Continued)

*Primary Examiner* — Moazzam Hossain
(74) *Attorney, Agent, or Firm* — Fish & Richardson P.C.

(57) ABSTRACT

A method of making a portion of a microfluidic channel includes lithographically patterning a first pattern into a first layer of photoresist disposed on a substrate, the first pattern representative of morphology of a reservoir rock; etching the first pattern into the substrate to form a patterned substrate; disposing a second layer of photoresist onto the patterned substrate; lithographically patterning a second pattern into the second layer of photoresist to reveal portions of the patterned substrate; and depositing calcite onto the exposed portions of the patterned substrate.

14 Claims, 3 Drawing Sheets

(56) References Cited

U.S. PATENT DOCUMENTS

| | | | |
|---|---|---|---|
| 2004/0146803 A1 | 7/2004 | Kohl et al. | |
| 2008/0246052 A1 | 10/2008 | Hsu | |
| 2009/0104564 A1* | 4/2009 | Yang | H01L 21/0338 430/312 |
| 2010/0330721 A1 | 12/2010 | Barlocchi et al. | |
| 2011/0123771 A1 | 5/2011 | Stavis et al. | |
| 2013/0236698 A1 | 9/2013 | Stavis et al. | |
| 2013/0316329 A1 | 11/2013 | Yu | |
| 2016/0023904 A1* | 1/2016 | Hart | B81C 1/00626 428/57 |
| 2016/0363600 A1 | 12/2016 | Sniadecki et al. | |
| 2017/0067836 A1 | 3/2017 | Hull | |
| 2017/0114242 A1 | 4/2017 | Lloyd et al. | |
| 2019/0324176 A1 | 10/2019 | Colburn et al. | |

FOREIGN PATENT DOCUMENTS

| | | |
|---|---|---|
| WO | WO 2018085782 | 5/2018 |
| WO | WO 2019032903 | 2/2019 |

OTHER PUBLICATIONS

Goo Lee et al., "Site-Selective in Situ Grown Calcium Carbonate Micromodels with Tunable Geometry, Porosity, and Wettability," Advanced Functional Materials, 2016, 26 (27), 10 pages.

Lee et al., "Site-Selective in Situ Grown Calcium Carbonate Micromodels with Tunable Geometry, Porosity and Wettability," Advanced Functional Materials, vol. 26, Jul. 1, 2016, 10 pages.

Lifton, "Microfluidics: an enabling screening technology for enhanced oil recovery (EOR)," Lab on a Chip, Royal Society of Chemistry, vol. 16, vol. 10, May 21, 2016, 20 pages.

Nilsen et al., "Growth of Calcium Carbonate by the Atomic Layer Chemical Vapour Deposition Technique," Thin Films. 2004, 450 (2), 8 pages.

Ren et al., "Materials for Microfluidic Chip Fabrication," Accounts of Chemical Research, Nov. 2013, 46 (11), 12 pages.

Sander et al., "Template-Assisted Fabrication of Dense, Aligned Arrays of Titania Nanotubes with Well-Controlled Dimensions of Substrates," Advanced Materials, vol. 16, No. 22, Nov. 18, 2004, 6 pages.

Song et al., "Chip-off-the-old-rock: the Study of Reservoir-Relevant Geological Processes with Real-Rock Micromodels," Lab on a Chip, Royal Society of Chemistry, 2014, vol. 14, 9 pages.

Spende et al., "TiO2, SiO2, and Al2O3 coated nanopores and nanotubes produced by ALD in etched ion-track membranes for transport measurements," Nanotechnology, vol. 26, Aug. 2015, 12 pages.

Zheng et al., "Surface Effect on Oil Transportation in Nanochannel: a Molecular Dynamics Study," Nanoscale Research letters, vol. 12, No. 1, Jun. 15, 2017, 9 pages.

PCT International Search Report and Written Opinion in International Appln. No. PCT/US2021/013,298, dated May 11, 2021, 14 pages.

* cited by examiner

CALCITE CHANNEL STRUCTURES WITH HETEROGENEOUS WETTABILITY

BACKGROUND

Crude oil deposits are often found in carbonate reservoir rock, such as limestone or dolostone. Interactions among fluids, such as brine and oil, and the reservoir rock can affect the flow of oil in the reservoir rock formations, for instance, during recovery of crude oil.

SUMMARY

The microfluidic and nanofluidic devices described here have fluid flow channels defined by calcite channel structures. The calcite channel structures have a surface morphology that is representative of morphological features of reservoir rock. For instance, the surface morphology of the calcite channel structures can be defined by images of real reservoir rock. The calcite channel structures have heterogeneous wettability, such as hydrophobic regions that are coated in a layer of calcite alternating with hydrophilic regions, such that the calcite channel structures can provide a reasonable approximation of realistic reservoir conditions. Visualization of fluid flow through these microfluidic devices, including visualization of fluid interaction with the hydrophobic and hydrophilic regions of the calcite channel structures, enables observation of the interactions of fluid, such as brine, with regions of differing wettability.

These visualizations can provide an understanding of the interaction between oils and brines under realistic reservoir conditions. For instance, wettability of reservoir rock by fluid can change depending on ionic composition and strength of the fluid; visualization of fluidic interactions with various wettability characteristics can provide an understanding of fluid-rock interactions under differing conditions. Understanding of these interactions can enable improvement of oil recovery processes in the field.

In an aspect, a method of making a portion of a microfluidic channel includes lithographically patterning a first pattern into a first layer of photoresist disposed on a substrate, the first pattern representative of morphology of a reservoir rock; etching the first pattern into the substrate to form a patterned substrate; disposing a second layer of photoresist onto the patterned substrate; lithographically patterning a second pattern into the second layer of photoresist to reveal portions of the patterned substrate; and depositing calcite onto the exposed portions of the patterned substrate.

Embodiments can include any combination of one or more of the following features.

The method includes generating a lithography mask according to an image of the reservoir rock; and lithographically patterning the first pattern into the first layer of photoresist using the lithography mask.

Lithographically patterning the first pattern into the first layer of photoresist includes: exposing the first layer of photoresist to energy according to the first pattern; and developing exposed portions of the first layer of photoresist. Exposing the first layer of photoresist to an energy beam includes exposing the first layer of photoresist to an electron beam.

Etching the first pattern into the substrate includes dry etching the first pattern into a silicon substrate.

Lithographically patterning the second pattern into the second layer of photoresist includes: exposing the second layer of photoresist to an energy beam according to the second pattern; and developing the exposed portions of the second layer of photoresist to reveal the portions of the patterned substrate. The method includes removing remaining portions of the second layer of photoresist after depositing the calcite. The method includes removing the remaining portions of the second layer of photoresist by a lift-off process.

Lithographically patterning a second pattern into the second layer of photoresist includes patterning a regular geometric pattern into the second layer of photoresist. Lithographically patterning a second pattern into the second layer of photoresist includes patterning a checkerboard pattern into the second layer of photoresist.

The method includes depositing calcite by atomic layer deposition (ALD).

Depositing calcite onto the exposed portions of the patterned substrate includes rendering the exposed portions of the patterned substrate hydrophobic.

Portions of the patterned substrate without deposited calcite are hydrophilic.

The method includes forming a microfluidic device including the microfluidic channel.

In an aspect, a microfluidic device includes a calcite channel structure defining at least a portion of a microfluidic channel. The calcite channel structure includes a substrate, a top surface of the substrate formed in a pattern representative of morphology of a reservoir rock; and a calcite coating disposed on first portions of the top surface of the substrate. The first portions are hydrophobic and second portions of the top surface of the substrate are hydrophilic.

Embodiments can include any combination of one or more of the following features.

The microfluidic device includes a housing, in which the calcite channel structure is disposed in the housing. The microfluidic device includes a fluid inlet and a fluid outlet defined in the housing and in fluid communication with the microfluidic channel. The microfluidic device includes a window in the housing, in which the window is optically transparent or transparent to electrons or both, in which the window is aligned with at least a portion of the calcite channel structure.

The first portions and second portions of the top surface of the substrate define a regular geometric pattern. The first portions and second portions of the top surface of the substrate define a checkerboard pattern.

The details of one or more implementations are set forth in the accompanying drawings and the description below. Other features and advantages will be apparent from the description and drawings, and from the claims.

DETAILED DESCRIPTION

Figure 1:
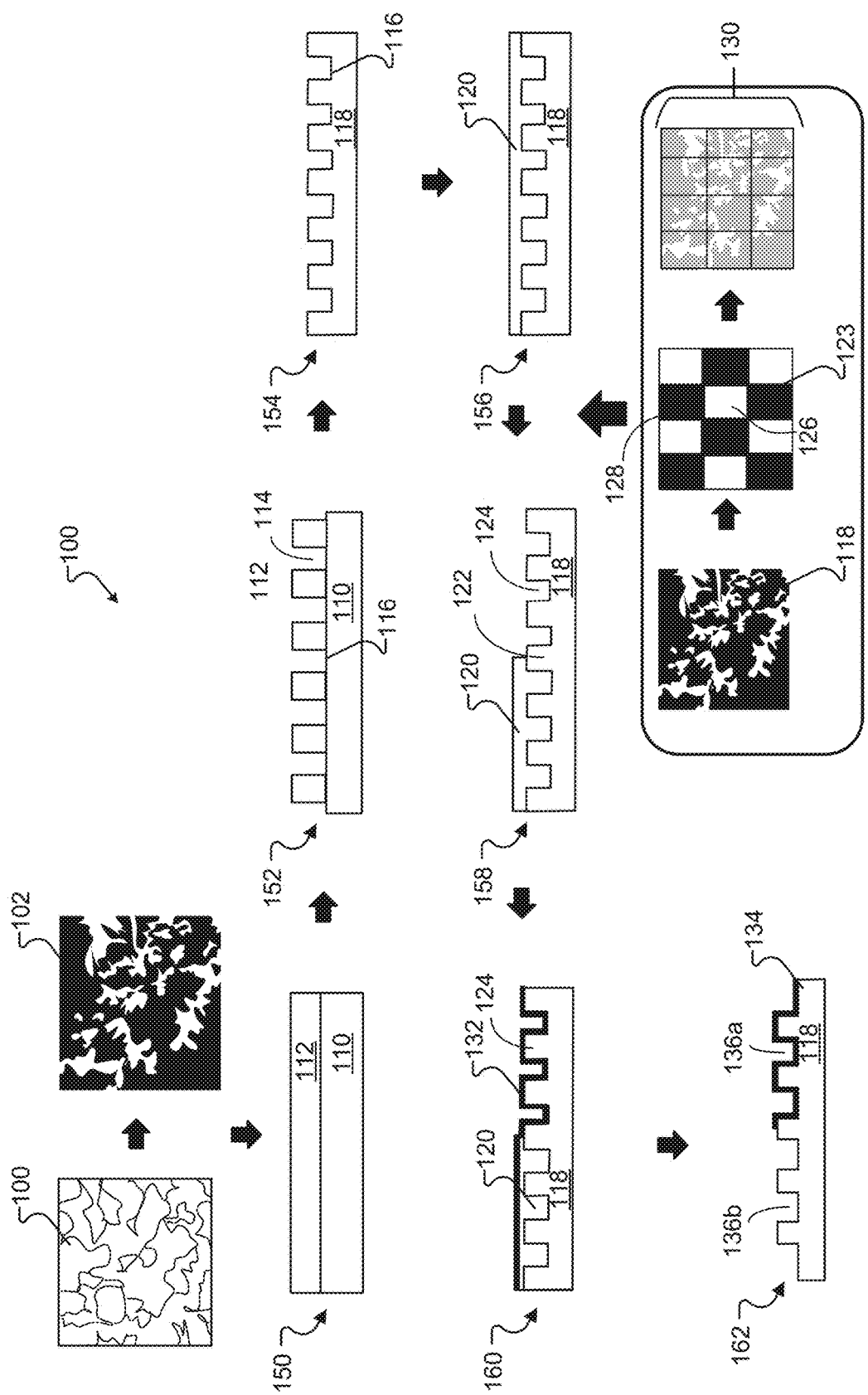
FIG. 1 is a process flow diagram.

Many crude oil reserves exist in carbonate reservoir rock formations such as limestone and dolostone. An understanding of the interactions among fluids, such as crude oil and brine, with these reservoir rock formations, particularly at small size scales such as the nanoscale, can be useful in designing systems for uniform and efficient flow of crude oil from these reservoir rock formations. This description relates to microfluidic or nanofluidic devices having channels with surface morphology and wettability characteristics that mimic environmental conditions in reservoir rock formations. The study of fluid, such as brine, flowing through these channels can be used to develop an understanding of the physical and chemical interactions of the fluid with the carbonate reservoir rock at the nanoscale.

The microfluidic and nanofluidic devices described here (referred to collectively as microfluidic devices) have fluid flow channels defined by calcite channel structures. The calcite channel structures have a surface morphology that is representative of morphological features of reservoir rock. For instance, the surface morphology of the calcite channel structures can be defined by images of real reservoir rock. The calcite channel structures have hydrophobic regions that are coated in a layer of calcite, alternating with hydrophilic regions, thus providing heterogeneous wettability characteristics of the calcite channel structures. Visualization of fluid flow through these microfluidic devices, including visualization of fluid interaction with the hydrophobic and hydrophilic regions of the calcite channel structures, enables observation of the interactions of fluid, such as brine, with regions of differing wettability. These visualizations can provide an understanding of the interaction between oils and brines under realistic reservoir conditions. For instance, wettability of reservoir rock by fluid can change depending on ionic composition and strength of the fluid; visualization of fluidic interactions with various wettability characteristics can provide an understanding of fluid-rock interactions under differing conditions.

The microfluidic devices here are fabricated by lithographic patterning of a substrate, such as a silicon substrate, according to a mask representative of morphological features of real reservoir rock. For instance, the mask can have been developed based on an image of real reservoir rock. A second patterning and deposition step provides for selective deposition of calcite on certain regions of the patterned substrate, with the other regions of the substrate remaining bare. The resulting structure is a substrate having a surface morphology representative of reservoir rock morphology, and with alternating regions of hydrophobicity and hydrophilicity. The structure can be used to define a portion of a fluid flow channel in a microfluidic device for observation, such as visualization, of fluid-rock interaction under differing wettability conditions.

Referring to FIG. 1, in an example process for generating a calcite channel structure for a microfluidic device, an image 100 of a reservoir rock, such as a carbonate reservoir rock, is obtained. For instance, the image 100 indicates the pore structure of the reservoir rock. The image 100 can be a scanning electron microscopy (SEM) image, an optical image, an atomic force microscopy (AFM) image, or another suitable type of image. The image 100 is converted into a lithography pattern mask 102, where the pattern of the lithography pattern mask is representative of features (such as morphological features) of the reservoir rock. For instance, the image 100 is converted to a black-and-white scale image using an image processing program, and the black-and-white scale image is used as a pattern by a laser writing system for mask fabrication. In some examples, the features of the reservoir rock have a size ranging from about 100 nm to about 100 μm.

A substrate 110 is coated with a photoresist 112 (cross-section 150). The substrate 110 can be silicon, quartz, glass, or another suitable material. The photoresist 112 can be a negative photoresist, such as polydimethylsiloxane (PDMS) or SU-8, or a positive photoresist. The photoresist 112 can be applied by spin coating, for instance, at a spin rate of between about 500 to about 2000 revolutions per minute. The spin rate determines the thickness of the layer of photoresist 112, which in turn contributes to the height of the resulting calcite channels. For instance, the layer of photoresist 112 can have a thickness between about 50-100 microns (μm). In some examples, the substrate 110 coated with the photoresist 112 is baked, for instance, at about 200° F.

The photoresist 112 is lithographically patterned according to the lithography pattern mask 102 to form a first pattern 114 in the photoresist 112, such that regions 116 of the underlying substrate 110 are revealed (cross-section 152). The first pattern 114 in the photoresist 112 corresponds to the pattern of the lithography pattern mask 102, which is representative of features, such as morphological features, of the reservoir rock.

Lithographic patterning of the photoresist 112 encompasses exposing the photoresist to energy, such as an electron beam (for electron beam lithography) or ultraviolet light (for photolithography), according to the lithography pattern mask 102. For instance, the electron beam can be provided by a scanning electron microscope (SEM). Lithographic patterning of the photoresist 112 encompasses developing the photoresist 112 after exposure. For positive photoresists, development removes the portions of the photoresist that were exposed to the energy beam. For negative photoresists, development removes the portions of the photoresist that were not exposed to the energy beam. Development of the photoresist 112 includes dissolving the photoresist using a solvent to reveal the regions 116 of the substrate 110. The solvent can be an organic solvent, such as propylene glycol methyl ether acetate (PGMEA), ethyl lactate, di-acetone alcohol, or another suitable solvent. After development, the substrate 110 and patterned photoresist 112 can be rinsed with a solvent, such as isopropyl alcohol, and dried with a gas, such as nitrogen.

The revealed regions 116 of the substrate 110 are etched using a dry or wet etching process to form a patterned substrate 118, and the remaining photoresist 112 is removed (cross-section 154). The pattern of the patterned substrate 118 corresponds to the pattern of the lithography pattern mask 102, and thus to features of the reservoir rock 100. The remaining, undeveloped portions of the photoresist 112 are removed, for instance, by dissolution with a solvent.

The patterned substrate 118 is coated with a second photoresist 120 (cross-section 156). The photoresist 120 can be a negative photoresist or a positive photoresist. The second photoresist 120 can be applied to the patterned substrate 118 as discussed supra for the photoresist 112.

The photoresist 120 is lithographically patterned according to a selective wettability pattern mask 123 to form a second pattern 122 in the photoresist 120 (cross-section 158). The selective wettability pattern mask 123 can define a regular geometric pattern of openings 126 and masked areas 128, such as a checkerboard pattern. Lithographic patterning of the photoresist 120 encompasses exposing the photoresist to an energy beam and developing the photoresist 120 after exposure, as described supra for photoresist 112. After lithographic patterning of the photoresist 120, regions 124 of the underlying patterned substrate 118 are revealed, with the second pattern 122 being superimposed 130 on the patterned substrate 118.

A layer of a hydrophobic material, such as calcite 132 (calcium carbonate; $CaCO_3$), silica ($SiO_2$), or alumina ($Al_2O_3$), is deposited onto the patterned photoresist 120 (cross-section 160). The calcite layer 132 is deposited onto both the revealed regions 124 of the underlying patterned substrate 118 and the photoresist 120 that remains after patterning. The calcite layer 132 can be deposited by a thin film deposition technique such as atomic layer deposition (ALD), chemical vapor deposition (CVD), physical vapor deposition (PVD), or another suitable deposition technique; or can be grown by an in situ growth technique. In an example, the calcite layer 132 is deposited by ALD at a deposition temperature of between about 200° C. and about 300° C., with an ozone gas flow of about 500 cm$^3$ min$^{-1}$, and with an applied sublimation temperature for calcium of about 195° C. The reactor pressure is maintained at about 1.8 mbar by employing a nitrogen carrier-gas flow of 300 cm$^3$ min$^{-1}$, supplied from a Nitrox 3001 nitrogen purifier with a purity of 99.9995% inert gas, such as N$_2$qAr. In some examples, the thickness of the calcite layer is about 50 nanometers (nm).

After deposition of the calcite layer 132, the photoresist 120 is removed (cross-section 162). For instance, the photoresist 120 is removed using a lift-off process in which the remaining photoresist 120 is dissolved by a solvent, causing removal of both the remaining photoresist 120 and the calcite layer 132 that is disposed on the remaining photoresist 120. Removal of the photoresist 120 results in a patterned substrate surface 134 having regions with the calcite layer 132 (such as a region 136a) and regions without calcite (such as a region 136b). The patterned substrate surface 132 has a surface morphology that is representative of the morphology of the reservoir rock and has alternating regions 136a of hydrophobicity, where the calcite is present, and regions 136b of hydrophilicity, where the calcite is not present. In some examples, the regions 136a of hydrophobicity occupy at least 50% of the surface area of the substrate surface 134. In some examples, the regions 136a and 136b form a regular pattern; in some examples, the regions 136a and 136b are randomly positioned.

Figure 2:
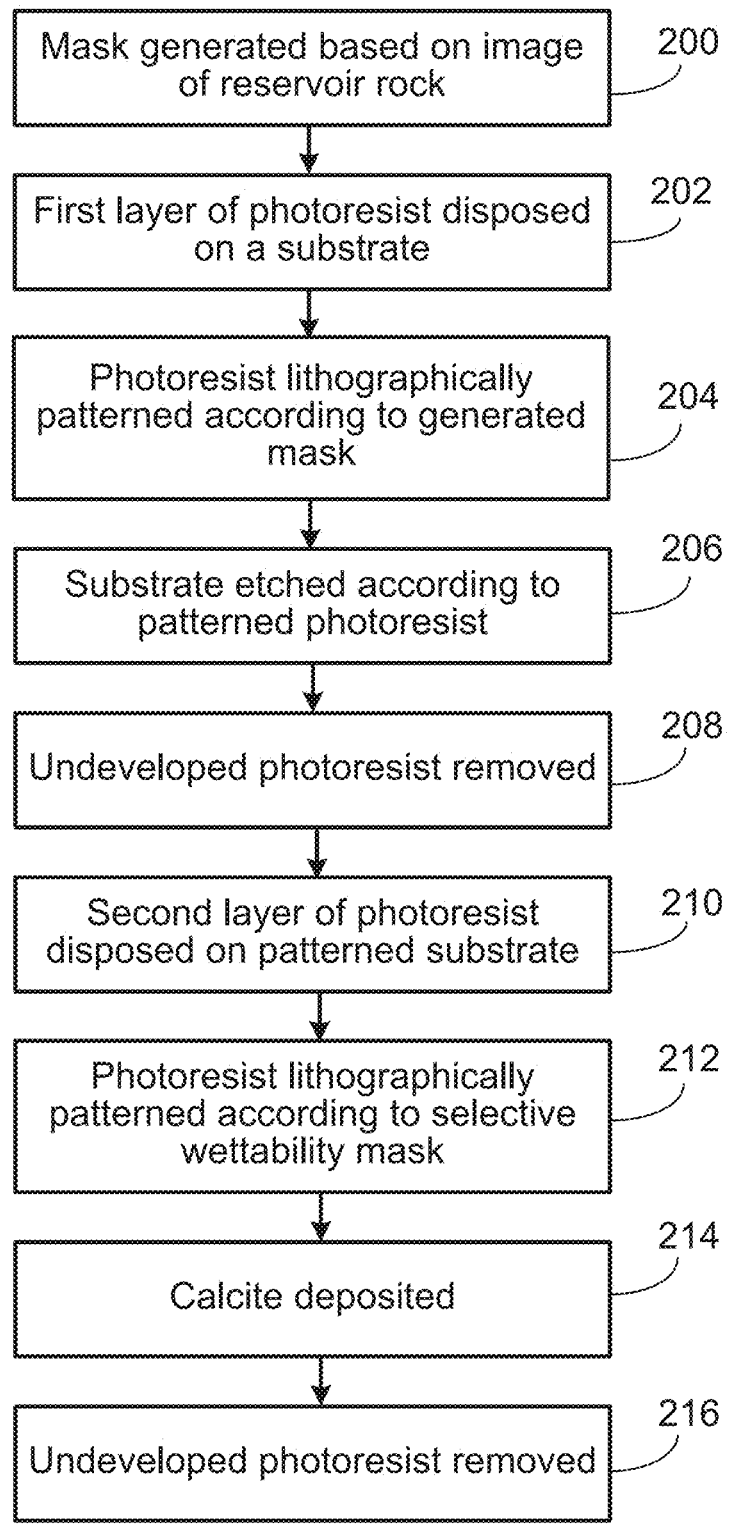
FIG. 2 is a flow chart.

Referring to FIG. 2, in an example process for fabricating a calcite channel structure, a lithography mask is generated according to an image of a reservoir rock (200). A first layer of photoresist is disposed on a substrate (202), for instance, by spin coating. The first layer of photoresist is lithographically patterned according to the lithography mask to form a first pattern in the first layer of photoresist (204), with the first pattern being representative of the morphology of the reservoir rock. Lithographic patterning of the first layer of photoresist includes exposing the first layer of photoresist to energy, such as an electron beam or ultraviolet light, according to the lithography mask; and developing exposed portions or unexposed portions of the first layer of the photoresist to reveal portions of the substrate underlying the developed portions of the first layer of photoresist. The first pattern is etched, such as dry etched, into the substrate to form a patterned substrate (206) representative of the morphology of the reservoir rock. The remaining, undeveloped portions of the first layer of photoresist are removed (208).

A second layer of photoresist is disposed on the substrate (210). The second layer of photoresist is lithographically patterned according to a selective wettability mask to form a second pattern in the second layer of photoresist (212), thereby revealing portions of the patterned substrate underlying the second layer of photoresist. Lithographic patterning of the second layer of photoresist includes exposing the second layer of photoresist to energy, such as an electron beam or ultraviolet light, according to the selective wettability mask; and developing exposed portions or unexposed portions of the second layer of the photoresist to reveal the portions of the patterned substrate underlying the developed portions of the second layer of photoresist. The selective wettability mask can define a regular geometric pattern, such as a checkerboard pattern.

Calcite is deposited onto the exposed portions of the patterned substrate (214) and onto the remaining, undeveloped portions of the second layer of photoresist. For instance, the calcite can be deposited by atomic layer deposition (ALD). The remaining, undeveloped portions of the second layer of photoresist are removed (216), which results in the removal also of the calcite disposed on those remaining portions of the second layer of photoresist. For instance, the remaining, undeveloped portions of the second layer of photoresist can be removed by a lift-off process. The resulting calcite channel structure has a surface morphology that is representative of the morphology of the reservoir rock based on which the lithography mask was generated, and has regions of alternating wettability: calcite coated regions are hydrophobic, and regions without calcite, which have a surface of exposed silicon substrate, are hydrophilic.

Figure 3:
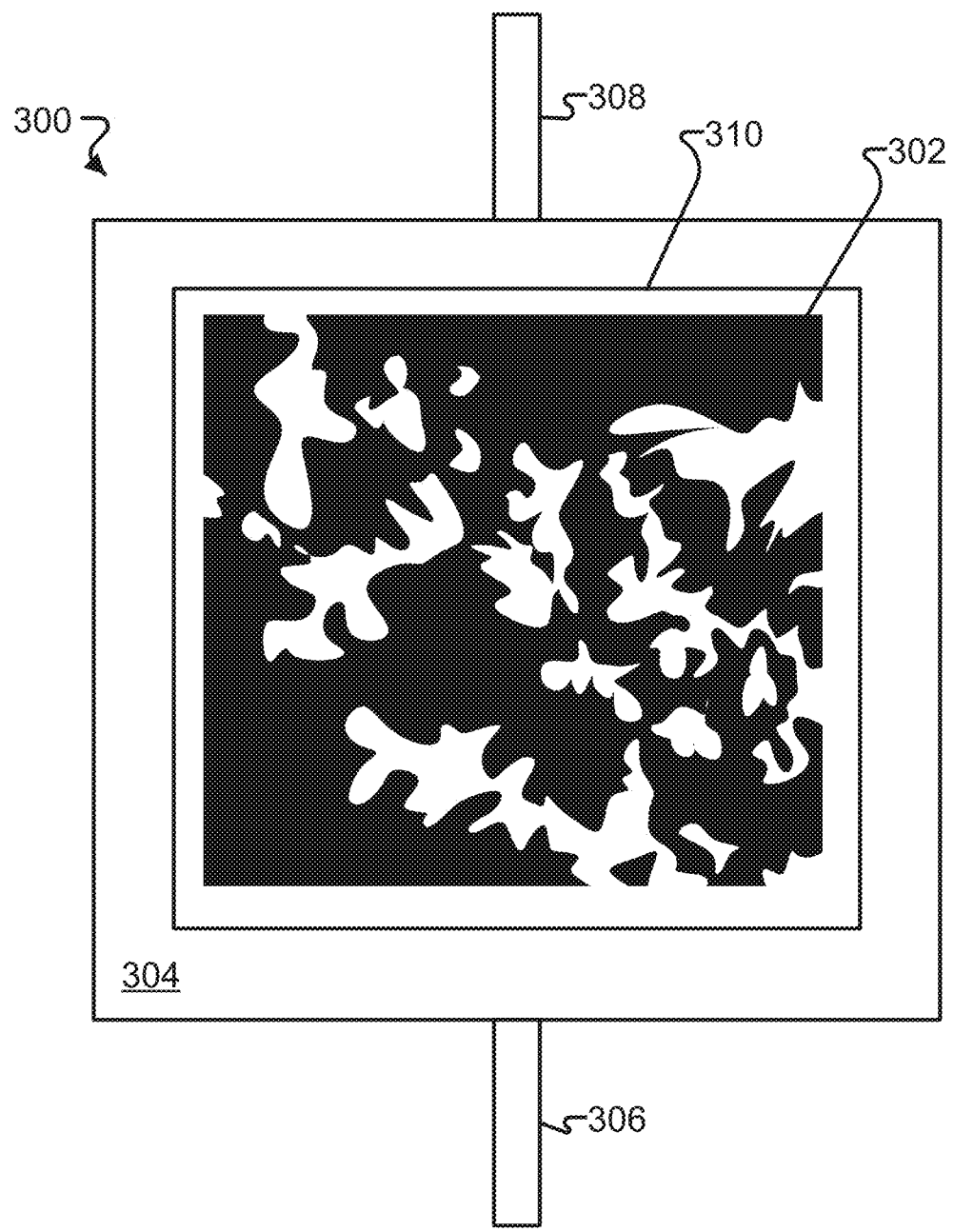
FIG. 3 is a diagram of a microfluidic device.

Referring to FIG. 3, a calcite channel structure 302 can be incorporated into a microfluidic device 300. The calcite channel structure 302 has a surface morphology representative of the morphology of the reservoir rock and has heterogeneous wettability. The calcite channel structure 302 is packaged in a housing 304 that has an inlet 306 and an outlet 308 such that fluid, such as brine, can flow in via the inlet 306, over the surface of the calcite channel structure 302, and out via the outlet 308. Interactions of the fluid with the surface of the calcite channel structure 302 can be observed to characterize the interaction of fluid with a realistic structure of calcite reservoir rock. The alternating regions of hydrophobicity and hydrophilicity on the surface of the calcite channel structure 302 provide heterogeneous wettability distribution that mimics wettability conditions in a real reservoir rock environment. In some examples, the microfluidic device 300 includes a window 310 generally aligned with the surface of the calcite channel structure 302 such that the interactions of the fluid with the surface of the calcite channel structure 302 can be observed visually. The window 310 can be optically transparent, to enable optical imaging of the fluid-substrate interactions; or transparent to an electron beam, to enable electron microscopy imaging of the fluid-substrate interactions; or both. The window 310 can be electrically conductive to avoid accumulation of electrical charge.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

We claim:

1. A method of making a portion of a microfluidic channel, the method comprising:
lithographically patterning a first pattern into a first layer of photoresist disposed on a substrate, the first pattern representative of morphology of a reservoir rock;
etching the first pattern into the substrate to form a patterned substrate;
disposing a second layer of photoresist onto the patterned substrate;
lithographically patterning a second pattern into the second layer of photoresist to reveal portions of the patterned substrate; and depositing calcite onto the exposed portions of the patterned substrate.

2. The method of claim 1, comprising:
generating a lithography mask according to an image of the reservoir rock; and
lithographically patterning the first pattern into the first layer of photoresist using the lithography mask.

3. The method of claim 1, in which lithographically patterning the first pattern into the first layer of photoresist comprises:
exposing the first layer of photoresist to energy according to the first pattern; and
developing exposed portions of the first layer of photoresist.

4. The method of claim 3, in which exposing the first layer of photoresist to an energy beam comprises exposing the first layer of photoresist to an electron beam.

5. The method of claim 1, in which etching the first pattern into the substrate comprises dry etching the first pattern into a silicon substrate.

6. The method of claim 1, in which lithographically patterning the second pattern into the second layer of photoresist comprises:
exposing the second layer of photoresist to an energy beam according to the second pattern; and
developing the exposed portions of the second layer of photoresist to reveal the portions of the patterned substrate.

7. The method of claim 6, comprising removing remaining portions of the second layer of photoresist after depositing the calcite.

8. The method of claim 7, comprising removing the remaining portions of the second layer of photoresist by a lift-off process.

9. The method of claim 1, in which lithographically patterning a second pattern into the second layer of photoresist comprises patterning a regular geometric pattern into the second layer of photoresist.

10. The method of claim 9, in which lithographically patterning a second pattern into the second layer of photoresist comprises patterning a checkerboard pattern into the second layer of photoresist.

11. The method of claim 1, comprising depositing calcite by atomic layer deposition (ALD).

12. The method of claim 1, in which depositing calcite onto the exposed portions of the patterned substrate comprises rendering the exposed portions of the patterned substrate hydrophobic.

13. The method of claim 1, in which portions of the patterned substrate without deposited calcite are hydrophilic.

14. The method of claim 1, comprising forming a microfluidic device including the microfluidic channel.

* * * * *